(12) United States Patent
Goldstein et al.

(10) Patent No.: US 7,368,166 B2
(45) Date of Patent: May 6, 2008

(54) POLYMERASE CHAIN REACTION USING METALLIC GLASS-COATED MICROWIRE

(75) Inventors: Alan H. Goldstein, San Francisco, CA (US); William C. LaCourse, Alfred, NY (US); Howard H. Liebermann, Succasunna, NJ (US)

(73) Assignee: Demodulation, Inc., Westwood, NJ (US)

( * ) Notice: Subject to any disclaimer, the term of this patent is extended or adjusted under 35 U.S.C. 154(b) by 24 days.

(21) Appl. No.: 11/098,052

(22) Filed: Apr. 4, 2005

(65) Prior Publication Data

US 2005/0221365 A1  Oct. 6, 2005

Related U.S. Application Data (60) Provisional application No. 60/559,995, filed on Apr. 6, 2004.

(51) Int. Cl.
  *B32B 15/00* (2006.01)
  *H01B 3/10* (2006.01)
  *B05D 5/12* (2006.01)

(52) U.S. Cl. ............... 428/379; 428/375; 428/389; 174/110 A; 148/110; 427/171; 427/120

(58) Field of Classification Search ............ 428/375, 428/379, 389, 384, 392, 433, 469; 148/110, 148/304; 174/110 A; 427/120, 126.2, 171
See application file for complete search history.

(56) References Cited

U.S. PATENT DOCUMENTS

| | | | | |
|---|---|---|---|---|
| 3,615,773 | A | * 10/1971 | Obidina et al. | ............... 501/63 |
| 5,240,066 | A |   8/1993 | Gorynin et al. | ............ 164/461 |
| 6,270,591 | B2 |   8/2001 | Chiriac et al. | ............. 148/300 |
| 6,544,193 | B2 |   4/2003 | Abreu | ........................ 600/558 |

OTHER PUBLICATIONS

Saiki, R.K. et al., Primer-directed Enzymatic Amplification of DNA with Thermostable DNA Polymerase, *Science 239* (1988) pp. 487-491.

* cited by examiner

*Primary Examiner*—Jill Gray
(74) *Attorney, Agent, or Firm*—Ernest D. Buff & Associates, LLC; Ernest D. Buff; Gordon E. Fish (57) ABSTRACT

A metallic glass-coated microwire has controllable surface porosity. The porosity is achieved by etching the metallic glass-coated microwire or other shapes of glass-coated bodies with acid after annealing to produce a multi-phase glass coating. Porous metallic glass-coated microwires are found to make superior PCR machines, which find use in a variety of in vivo, biochemical, and chemical sensors. Advantageously, the PCR apparatus is smaller, less expensive to construct than conventional units. It readily carries out in vivo passive or active operations.

20 Claims, 3 Drawing Sheets

POLYMERASE CHAIN REACTION USING METALLIC GLASS-COATED MICROWIRE

RELATED U.S. APPLICATION DATA

This application claims the benefit of U.S. Provisional Application No.: 60/559,995, filed Apr. 6, 2004.

BACKGROUND OF THE INVENTION

1. Field of the Invention

This invention relates to the use of metallic glass-coated microwire (MGCM) in support of a polymerase chain reaction (PCR); and more particularly, to a micro-scale, self-contained PCR system that is capable of conducting the PCR (or an RT-PCR) reaction, detecting PCR products, and transmitting a signal that indicates whether or not a nucleic acid amplification event has occurred.

2. Description of the Prior Art

The genetic material of each living organism, whether plant or animal, bacterium or virus, possesses sequences of its nucleotide building blocks (usually DNA, sometimes RNA) that are uniquely and specifically present only in its own species. Indeed, complex organisms such as human beings possess DNA sequences that are uniquely and specifically present only in particular individuals. These unique variations make it possible to trace genetic material back to its origin, identifying with precision the species of the organism from which the genetic material came; and oftentimes the particular member of that species.

Such an investigation requires, however, that enough of the DNA under study is available for analysis, which is the issue that PCR addresses. PCR [R. K. Saiki, et. al., "Primer-directed Enzymatic Amplification of DNA with Thermostable DNA Polymerase", Science 239 (1988) pp. 487-491] exploits the remarkable natural function of the enzymes known as polymerases. These enzymes are present in all living things, and their function is to copy genetic material and also to then proofread and correct the copies. PCR can characterize, analyze, and synthesize a specific piece of DNA or RNA. It works even on extremely complicated mixtures, seeking out, identifying, and duplicating a particular bit of genetic material from blood, hair, or tissue specimens, from microbes, animals, or plants, some of them many thousands, or possibly even millions of years old.

PCR requires a template molecule (the DNA or RNA to be copied) and two primer molecules to get the process started. These primers, called nucleotides or bases, are short chains of the four different chemical components that make up any strand of genetic material. DNA itself is a chain of nucleotides. Under most conditions, DNA is double-stranded, consisting of two such nucleotide chains that wind around each other in what is commonly known as a double helix. Primers are single-stranded. They consist of a string of nucleotides in a specific sequence that will, under the right conditions, bind to a specific complementary sequence of nucleotides in another piece of single-stranded RNA or DNA. For PCR, primers must be duplicates of nucleotide sequences on either side of the piece of DNA of interest, which means that the exact order of the primers' nucleotides must already be known. These flanking sequences can be constructed in a laboratory or purchased from commercial suppliers.

There are three basic steps in PCR. First, the target genetic material must be denatured; that is, the strands of its helix must be unwound and separated by heating to 90-96° C. The second step is hybridization or annealing, in which the primers bind to their complementary bases on the now single-stranded DNA. The next step is DNA synthesis by a polymerase. Starting from the primer, the polymerase can read a template strand and match it with complementary nucleotides very quickly. The result is then two new helixes in place of the first, each composed of the original strands plus its newly assembled complementary strand.

All that PCR requires in the way of equipment is a reaction tube, reagents, and a source of heat. Different temperatures have been found to be optimal for each of the three steps in the PCR reaction. Thus, commercial PCR machines have been developed to automatically control these temperature regimes automatically.

To get more of the DNA desired, the process is simply repeated by denaturing the DNA that has already been made. The amount of DNA will double with every processing cycle, each of which takes only 1-3 minutes so that repeating the process for just 45 minutes can generate hundreds of millions (usually billions) of copies of a specific DNA strand. Once the primers have been characterized and obtained, PCR can do, in one week, work that used to be technically impossible (e.g. the cloning of a single copy DNA molecule).

One of the most troublesome technical problems encountered with PCR involves contamination of the sample with extraneous genetic material, thereby generating numerous copies of irrelevant DNA. When such contamination occurs, the resulting product is rendered useless; and oftentimes leads erroneous conclusions. Preventing contamination is of particular importance in human applications, such as medicine or the law, in which someone's life may literally hang in the balance. Likewise, security and defense applications will require a very low number of 'false positive' events. For example, mistaken activation of a PCR-based bioweapons sensor could result in mobilization of defense forces or heighten public anxiety due to inaccurate information predicting a bioweapons-based attack.

SUMMARY OF THE INVENTION

The present invention provides MGCM having a porous glass surface, and a process for its production. Porosity dimensions are generally in the 50-100 nm range. Larger-sized porosity is obtained by a suitable choice of heat treatment times and temperatures. In addition, the invention provides a method and apparatus for conducting PCR in a highly versatile manner. This is accomplished by using the unique properties of the MGCM to create a single device that incorporates the functions of two devices and a biochemical reaction. The two devices are the PCR machine (a.k.a. thermal cycler) and a device for detection of the DNA produced by the DNA reaction. Currently, this DNA is detected via optical or fluorescent methods after the PCR product has been removed from the thermal cycler. Advantageously, it has been found that the use of metallic glass-coated microwire in the PCR process enables a significant reduction in size (approximately from that of a microwave oven to that of a wire), thereby greatly enhancing utility. The co-axial structure of metallic glass-coated microwire allows precise temperature control for each individual microwire segment because the metallic core is now used as an heating element that is activated either by the application of an electrical potential difference between the ends of the microwire, or by the application of a suitable alternating magnetic field to cause temperature rise and stabilization via eddy currents in the metallic core of the microwire on which PCR occurs. Utilizing this basic concept, various forms of genome diagnosis and even therapy are envisioned. The ability to conduct PCR and sense gene amplification in micro-scale glass fibers has enormous commercial potential in in vivo diagnostics during medical procedures or medical testing. For medical diagnostics and sensor applications, arrays of microwire offer the opportunity to do massively parallel sample analyses. The electrically active component of the system may drive electroporation, combining in situ amplification and delivery of specific genes (gene therapy). The same ability to do in situ delivery may be used to do in situ detection, possibly including the insertion of the microwire into individual target cells. This capability can lead to incorporation of the present invention into microsurgical devices for real-time analyses of tissues during medical procedures. Several enabling technologies are required, including special MGCM composition and cross-sectional geometry, as well as instrumentation for monitoring. Many biotech, medical, environmental and industrial sensing applications are envisioned and include commercial applications related to bio-catalysis, and bio separations.

In accordance with the invention, there is provided a composite device whereby the components of the PCR reaction are either: a) loaded or encapsulated into nano- or microporous glass that is part of the microwire itself; b) maintained at the surface via entrapment in a hydrogel-like layer. By placing the PCR reaction system near or at the surface of the MGCM, DNA target molecules, or DNA-containing systems may be acquired from the environment and the DNA so obtained will form the substrate for DNA amplification via PCR. A successful PCR event will also require thermal cycling to amplify the DNA and some form of detection of the DNA product. The MGCM system itself can act as the thermal cycling component of the PCR machine via induced heating and cooling. Detection can be accomplished photonically, spectrophotometrically or electromagnetically, based on the intrinsic properties of the glass and metal components of the system. The result of this invention is a micro-scale, self-contained PCR system that is capable of conducting the PCR (or the RT-PCR) reaction, detecting PCR products, and transmitting a signal that indicates whether or not a nucleic acid amplification event has occurred. This system is scalable, with the bundling of multiple MGCM wires or the 'bar-coding' of multiple sites on single microwires sufficient to create highly, or massively parallel systems.

Numerous, highly advantageous uses for glass-coated articles produced in accordance with the present invention are disclosed hereinafter in greater detail.

BRIEF DESCRIPTION OF THE DRAWINGS

The invention will be more fully understood and further advantages will become apparent when reference is had to the following detailed description and the accompanying drawings, in which.

DETAILED DESCRIPTION OF THE INVENTION

As used herein, the term "amorphous metallic alloy" means a metallic alloy that substantially lacks any long-range order and is characterized by x-ray diffraction intensity maxima that are qualitatively similar to those observed for liquids or oxide glasses. By way of contrast, the term "nanocrystalline metallic alloy" pertains to those metallic alloys having constituent grain sizes on the order of nanometers.

The term "ferromagnetic", as used herein, refers to a material that can possess magnetization in the absence of an external magnetic field.

The term "glass", as used throughout the specification and claims, refers to an inorganic product of fusion that has cooled to the solid state without crystallizing, or to glassy materials formed by chemical means such as a sol-gel process, or by "soot" processes, both of which are used to form glass preforms that are used in fiber optic processing. These materials are not fused; but rather are consolidated at high temperatures, generally below the fusion temperatures of the constituents in question.

The term "microwire", as used herein, refers to a thin element, which may be continuous or non-continuous, of circular or non-circular cross-section, and which has a transverse dimension less than about 50 μm.

The term "drawing", as used herein, refers to the extension of a material using a tensile force, the extension resulting in a permanent reduction of the material's cross-sectional area.

The term "preform", as used herein, means the glass vessel in which alloy is melted and drawing into a member.

The terms "liquidus temperature" and "liquidus", as used herein, refer to the temperature above which there exist no stable crystalline phases in the material.

The term "thermal contraction coefficient", as used herein, refers to the amount of length change of a material per unit length of that material, and per unit temperature, when the material is cooled from a high temperature to a low temperature.

The terms "working temperature" and "working point", as used herein, refer to the temperature at which a glass has a viscosity of $10^3$ Pa-sec.

The term "sol-gel", as used herein involves the transition of a system from a liquid "sol" (mostly colloidal) into a solid "gel" phase. Applying the sol-gel process, it is possible to fabricate ceramic or glass materials in a wide variety of forms.

The term "polymerase chain reaction", as used herein, refers to an enzymatic reaction system used to directly amplify (usually) rare specific DNA or RNA sequences in a complex mixture when the ends of the sequence are known. This method of amplifying rare sequences from a mixture is of great utility both for basic research and applied systems such as molecular diagnosis of diseases and disorders. The PCR system consists of a thermostable DNA-dependent DNA polymerase (with the addition of a second RNA-dependent DNA polymerase, a.k.a. reverse transcriptase for RT-PCR). In addition to the enzyme, the PCR reaction requires a standard set of reagents including deoxyribonucleotide triphosphates, Mg++, an appropriate buffering system, and primers that define the 5' ends of the double-stranded target molecule. The double stranded target molecule may be DNA or the RNA:DNA product of reverse transcriptase.

The term "primer", as used herein, refers to short oligonucleotide sequences that are sufficient homologous to the 5' termini of a double-stranded nucleic acid sequence so that they can hydrogen-bond to them via standard base pairing. The primer is then extended along the length of the target sequence via the intrinsic processivity of the polymerase enzyme. Primer extension is the basis of the DNA polymerase reaction regardless of whether it is a DNA-dependent DNA polymerase or an RNA-dependent DNA polymerase (reverse transcriptase).

The term "enzyme", as used herein, refers to any of various complex organic protein-based substances, originating from living cells and capable of producing certain chemical changes in organic substances by catalytic action.

The term "nucleotide", as used herein, refers to any of the class compounds formed by the hydrolysis of nucleic acids or nucleotides, consisting essentially of deoxyribose or ribose combined with adenine (A), or guanine (G) and cytosine (C), urasil (U), or thymine (T).

The term "DNA", as used herein, refers to any of the class of nucleic acids that contains deoxyribose, found chiefly in the nucleus of cells.

The term "RNA", as used herein, refers to any of the class of nucleic acids that contains ribose, found chiefly in the cytoplasm of cells.

The term "oncogene" as used herein refers to a gene that can cause, or at least is associated with cancer.

The term "prions", as used herein, refers to the only pathogen identified to date that does not have a genome. Prions are assumed to be self-catalyzing infectious protein particles.

The invention discloses means by which MGCM can be made to have a controlled porous glass surface, which can result from either immersion of the MGCM in selected acid baths or by exposure to suitable vapors. In fact, this approach is applicable to a variety of shapes, other than just wire. For example, glass-coated metallic sheet, tube, and other geometric forms can be made to have the porosity of the present invention. In different embodiments, the glass has at least 5%, 20%, or 50% surface porosity, as determined by its surface area. The amount and configuration of the surface porosity is defined by a plurality of pores in the glass surface. The physical mechanism by which porosity in the glass is created is by first obtaining a multi-phase glass in which at least one of the phases is removed by selective leaching. In order to produce a porous glass surface on MGCM incorporating a glass that does not separate into multiple phases upon heat treatment, a suitable glass having the desired response to heat treatment can be coated onto the MGCM using sol-gel or other processes.

The invention includes means by which the denaturization step of PCR is accomplished by heating of the MGCM. This can be achieved by the passing of an electrical current through the length of the MGCM metallic core. Alternatively, if the metallic core of the MGCM is ferromagnetic, then a high frequency magnetic field acting upon said metallic core can be used to remotely heat the MGCM.

The invention provides an article whereby the biochemical reagents and enzymes of the PCR reaction are encapsulated or loaded into nano- or microporous glass that is either a part of the as-drawn glass-coated metallic microwire or is deposited thereon by dipping, spraying, or some other method. These articles include the thermostable DNA polymerase, deoxyribonucleotide triphosphates (also known as nucleotides or dNTPs, the monomeric precursors of DNA), single-stranded primer DNA (ssDNA) primers specific for a given reaction and an aqueous buffer that includes $Mg^{++}$ and other components required for optimization of the reaction. An important aspect of fabrication is to create an encapsulated or loaded glass that retains the PCR mixture but allows entry of the double-stranded DNA (dsDNA) 'target' molecules. A number of possibilities exist. For example, the PCR mixture can be retained on the hydrated surface of micro- or nanopores until such time as the system is 'immersed' in a solution containing the dsDNA target. Depending on pore size, the external solution enters the pores by capillary action. The reaction is then initiated before any significant diffusional exchange could occur between the pores and the external medium. Once a few rounds of PCR have occurred, the solution would probably become too viscous for significant diffusion of the reaction mixture components. A second procedure involves physical isolation of the glass-coated metallic wire after it is been loaded with target DNA. This would be a design parameter of the article, rather than an intrinsic property of the glass itself. After the porous glass has been exposed to the external solution for 'DNA loading' some type of article design is implemented whereby the MGCM is "chambered" or otherwise sealed off at the surface so that no further exchange between the pores and the environment is possible. In addition, the invention offers a process whereby thermal cycling is induced in the MGCM, creating the appropriate reaction conditions for PCR.

Further, the invention provides a method whereby the PCR reaction may be detected. One of the advantages of the MGCM technology is that there is a multiplicity of ways to detect the dsDNA product of the PCR reaction. As a result of the geometric amplification achieved by the PCR process, 30 PCR cycles will produce ~1 billion DNA molecules from a single target. These molecules are both high molecular mass and highly polar due to the dual phosphodiester backbones of the 2 nucleic acid strands. Therefore, we may expect that, as the PCR reaction progresses, the pores of the glass will become filled with high molecular mass DNA, replacing the mixture of soluble monomeric dNTP precursors. DNA may be detected in a number of ways. For example, photonic methods include changes in fluorescence (if flurophore-labelled dNTPs are used), and changes in the characteristic absorbance of nucleic acids at 254-nm wavelength. In the latter case, the absorbance of the free dNTPs is much greater than that of the dsDNA due to the fact that the 254-nm absorbing moieties are buried in the interior of the double helix structure. This is the well-known, hyperchromic effect of DNA. The denaturation/renaturation or incorporation of free dNTPS into dsDNA can be monitored via hyper/hypochromic changes in absorbance at 254-nm. Both of these methods will be facilitated by the fact that the reaction in being conducted in glass.

Finally, the accumulation of the electrically highly polar material of PCR will have some isotropy due to the orientation of the long double-helical strands relative to one another. Therefore, some type of electromagnetic signal or change in the electromagnetic properties of the MGCM metallic core will be induced due to the effects of electromagnetic fields associated with the electrically polar nature of the material. In addition, the accumulation of this highly polar material will affect the properties of evanescent light waves passing through the glass, providing yet another means of monitoring the PCR process.

Applications of the present invention include but are not limited to: 1) Placement of the PCR reaction at specific locations inside the body or even inside specific tissues or individual cells via the MGCM technology; 2) Placement of the PCR reaction at precise locations in vitro where microscaling of the reaction will provide unique advantages. For example, as part of lab-chip systems for diagnostic or high-throughput drug discovery applications; 3) Creating micro-scale sensor systems that are environmentally 'rugged' due to the encapsulation of the PCR system in nano- or microporous glass. The unique aspect here is that the MGCM technology allows the PCR system to be self-contained insofar as thermal cycles can be induced directly using the MGCM technology. PCR offers the opportunity to create a Universal Detector for any life form that has either a DNA or RNA genome. That covers everything but prions.

The teaching of the present invention can be used in conjunction with metallic alloys having various compositions, whether such alloys are amorphous, nanocrystalline, or otherwise. The present invention can also be used with various kinds of glasses of which the preforms are made.

The following examples are presented to provide a more complete understanding of the invention. The specific techniques, conditions, materials, proportions and reported data set forth to illustrate the principles and practice of the invention are exemplary and should not be construed as limiting the scope of the invention.

EXAMPLE 1

Figure 1:
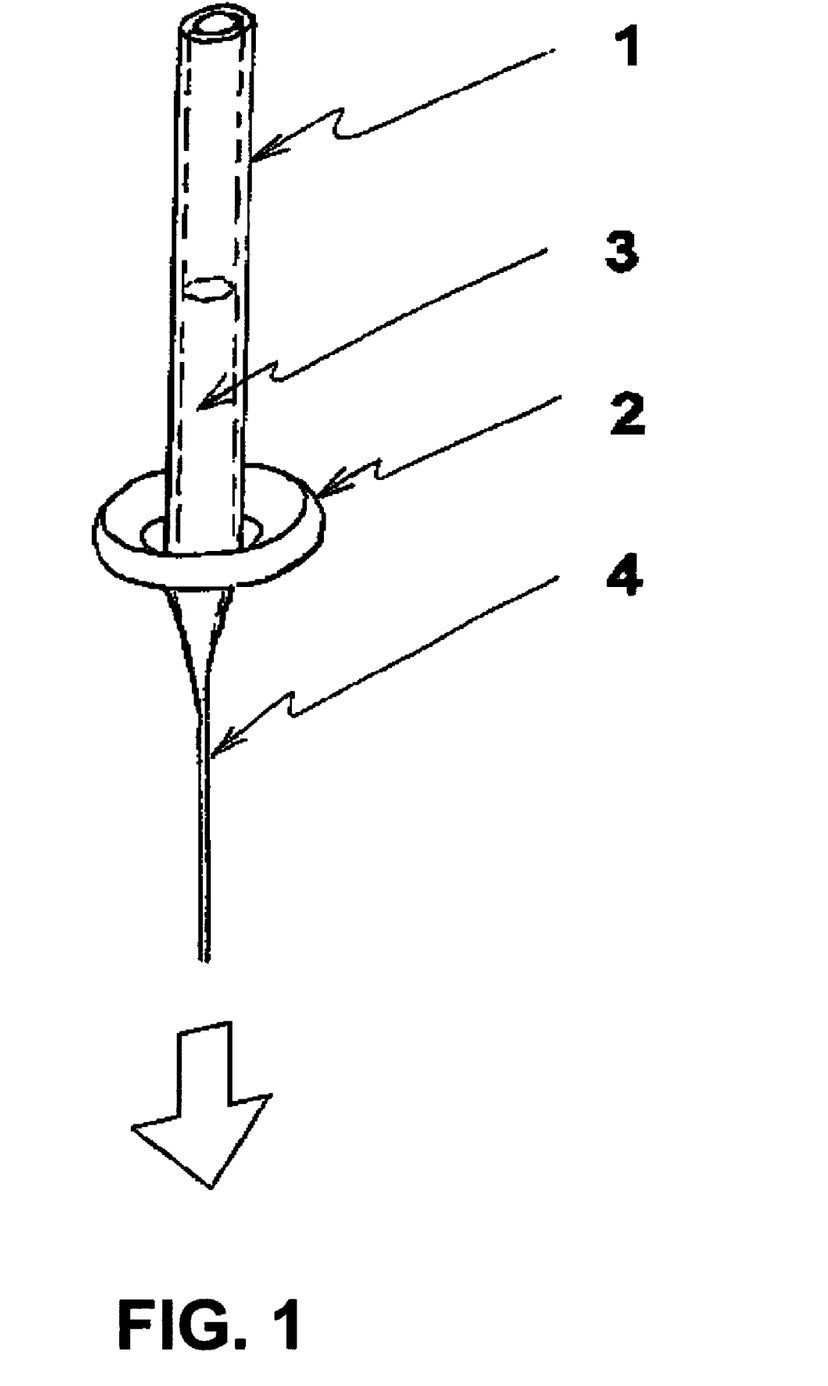
FIG. 1 is a perspective view showing metallic glass-coated microwire produced by drawing from a round glass tube.

An ingot composed of an amorphous-forming metallic alloy is prepared by loading the appropriate weights of constituent elements into a quartz tube that is sealed at one end. The other end of this quartz tube is connected to a pressure-vacuum system to allow evacuation and back filling with Ar gas several times to ensure a low oxygen Ar atmosphere within the quartz tube. Next, the closed end of the quartz tube in which the elements reside is introduced into a high frequency induction-heating coil. With the application of radio frequency ("r.f.") power, the elements inside the tube are caused to heat and melt into a stirred, homogeneous metallic alloy body. When the r.f. power is shut off, the alloy body is allowed to cool to room temperature in the Ar atmosphere. Once cooled, the same metallic alloy body is inserted into the bottom of a vertically disposed glass tube 1 (preform), having 6-mm diameter that is sealed at the lower end, as depicted in FIG. 1. The upper end of this preform is connected to a pressure-vacuum system to allow evacuation and back filling with Ar gas several times to ensure a low oxygen Ar atmosphere within the quartz tube. A specially built inductor 2 at the bottom of the preform is energized with r.f. power in order to heat and then melt the metallic alloy body 3 within the tube. Once the metallic alloy body is molten and sufficiently heated above its liquidus temperature, a solid glass rod is used to touch and bond to the bottom of the sealed glass preform in which the molten metallic alloy resides. The heat of the molten metallic alloy softens the glass preform allowing it to be drawn by pulling on the glass rod to which it is attached. Molten metallic alloy is entrained in the drawn glass capillary 4 that results. The drawn capillary is then pulled and guided onto a spinning take-up spool, which provides both winding tension to ensure continuous drawing at a rate of about 5 meters/second and a systematically wound article (microwire) package.

Amorphous glass-coated microwire about 30 µm in diameter is produced using the procedure described above. The microwire has a $Co_{66}Fe_4Ni_1B_{14}Si_{15}$ amorphous alloy core that is under axial tensile stress. The glass from which the preform was made, and which coats the microwire, is a low-expansion borosilicate having the approximate composition set forth below:

| Constituent | Weight % |
| --- | --- |
| $SiO_2$ | 60 |
| $B_2O_3$ | 33.5 |
| $Na_2O$ | 6.5 |
| Working Point | >1,150° C. |
| Assumed set point = Annealing Point = | 550° C. (depends on cooling rate) |
| Elastic Modulus | 80 GPa |
| $\alpha_{gl}$ (Annealing pt. − 25° C.) | 50 ppm ° $C.^{-1}$. |

The amorphous metallic alloy used to form the microwire has the following properties:

| Liquidus | 1,081° C. |
| --- | --- |
| Elastic Modulus | 200 GPa |
| $\alpha_a$ | 8.0 ppm ° $C.^{-1}$. |

The working point of this glass is slightly higher than the liquidus temperature of the metallic alloy, but within limits that allow easy article formation.

Figure 2:
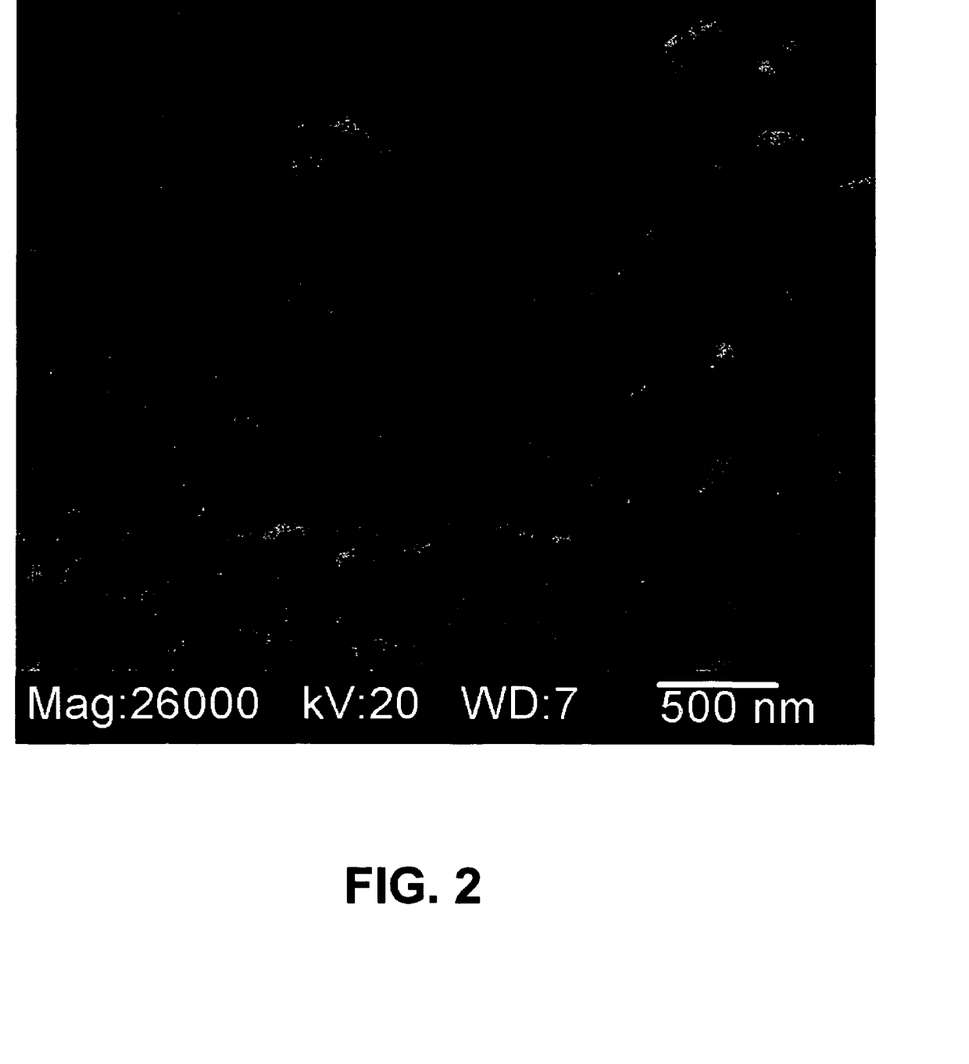
FIG. 2 is a scanning electron micrograph showing MGCM with $6.5Na_2O.33.5B_2O_3\text{-}60SiO_2$ glass coating surface microstructure, containing porosity after having been heat-treated and etched by immersion in acid solution, the dimensional scale of porosity being generally in the range 50-100 nm.

Subsequent to its manufacture, the MGCM is then heated for a time at temperature to result in a multi-phase microstructure of the glass and a dimensional scale that is commensurate with that of the level of porosity desired. Acid etching of the multi-phase glass in the MGCM will selectively remove the boric oxide ($B_2O_3$) phase, while the silica ($SiO_2$)— rich phase is nearly insoluble in the same acid mixture. A typical leached glass surface microstructure that results is shown in FIG. 2.

EXAMPLE 2

An ingot of copper is inserted into the bottom of a vertically disposed glass tube 1 (preform) that has a 6-mm diameter and is sealed at the lower end, as depicted in FIG. 1. The upper end of this preform is connected to a pressure-vacuum system to allow evacuation and back filling with Ar gas several times to ensure a low oxygen Ar atmosphere within the quartz tube. A specially built inductor 2 at the bottom of the preform is energized with r.f. power in order to heat and then melt the metallic alloy body 3 within the tube. Once the ingot is molten and sufficiently heated above its melting temperature, a solid glass rod is used to touch and bond to the bottom of the sealed glass preform in which the molten copper resides. The heat of the molten copper softens the glass preform, allowing it to be drawn by pulling on the glass rod to which it is attached. Molten copper is entrained in the drawn glass capillary 4 that results. The drawn capillary is then pulled and guided onto a spinning take-up spool, which provides both winding tension to ensure continuous drawing at a rate of about 5 meters/second and a systematically wound microwire package.

Metallic glass-coated microwire (MGCW) about 30 µm in diameter is produced using the procedure described above. The microwire has a copper core that is under axial tensile stress. The glass from which the preform was made, and which coats the microwire, is a low-expansion borosilicate having the approximate composition set forth below:

| Constituent | Weight % |
| --- | --- |
| $SiO_2$ | 60 |
| $B_2O_3$ | 33.5 |
| $Na_2O$ | 6.5 |

| | |
| --- | --- |
| Working Point | >1,150° C. |
| Assumed set point = Annealing Point = | 550° C. (depends on cooling rate) |
| Elastic Modulus | 80 GPa |
| $\alpha_{gl}$ (Annealing pt. – 25° C.) | 10 ppm ° $C.^{-1}$. |

The copper used to form the microwire has the following properties:

| | |
| --- | --- |
| Liquidus | 1,083° C. |
| Elastic Modulus | 130 GPa |
| $\alpha_a$ | 17.7 ppm ° $C.^{-1}$. |

The working point of this glass is higher than the melting temperature of the copper, but within limits that allow easy microwire formation.

Subsequent to its manufacture, the MGCM is then heated for a time at temperature to result in a multi-phase microstructure of the glass, and a dimensional scale that is commensurate with that of the level of porosity desired. Acid etching, at solution temperatures of 50-95° C., of the multi-phase glass in the MGCM will selectively remove the boric oxide ($B_2O_3$) phase, while the silica ($SiO_2$)— rich phase is nearly insoluble in the same acid mixture. A leached glass surface microstructure representative of that produced is shown in FIG. 2.

EXAMPLE 3

Figure 3:
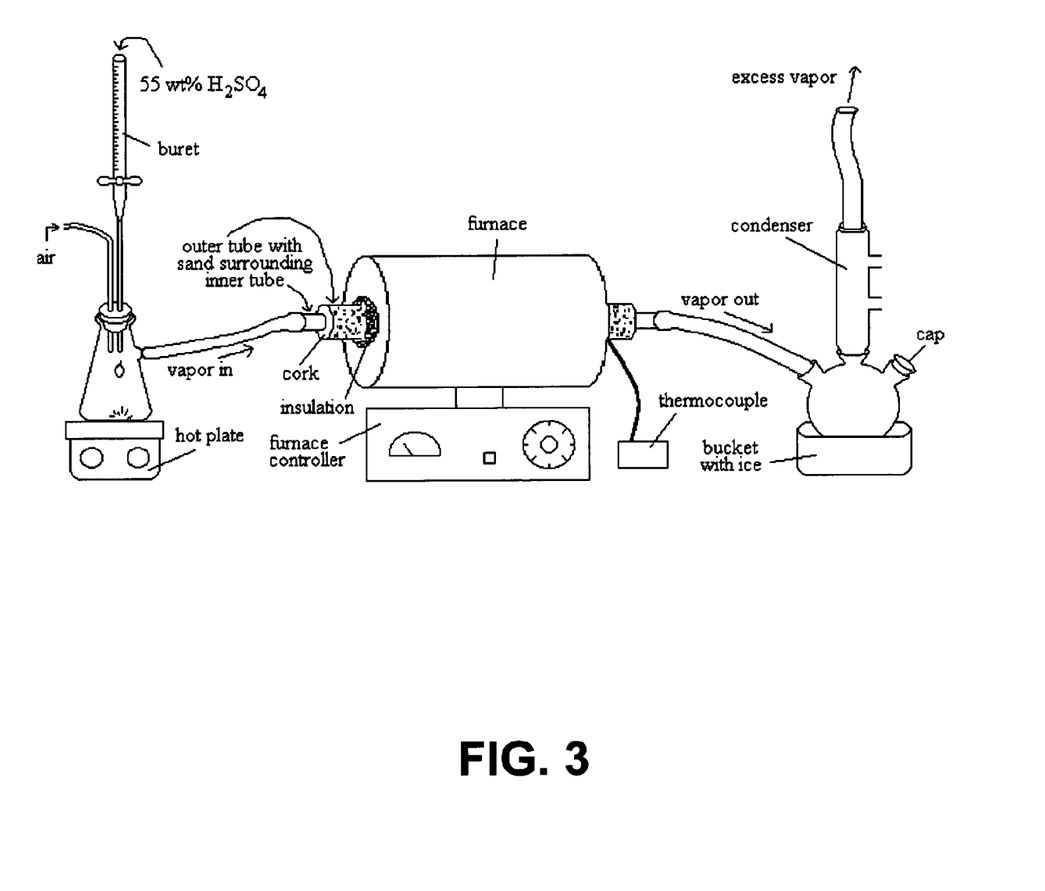
FIG. 3 is a schematic representation of a vapor etching process for producing porosity in MGCM.

MGCM having a copper core is produced per the procedure of Example 2. The post-drawing process, shown in FIG. 3, begins with 55 wt. % $H_2SO_4$ introduced into buret (1) to be followed by and evaporation flask 2 to which air 3 is also added. The acid/air mixture in this flask is heated using a hot plate 4 to create acid vapor, which is introduced into a thermally insulated oven 5 containing the MGCM for treatment at 550° C. for 30 minutes. Acid vapor is flowed continuously for the treatment time and is cleansed using a condenser 6 before being liberated 7. In the present example the glass surface is simultaneously transformed to have multiple phases and leached during the heat treatment during a single step operation.

EXAMPLE 4

Environmental biosensor application. The presence of *E. coli* in surface and other waters is diagnostic of fecal contamination and is used to monitor the sanitary conditions of streams, lakes, and the like. Multiple *E. coli* genomes have been completely sequenced and are available in public domain databases. While some genetic diversity exists, highly conserved sequences unique to *E. coli* form the basis of effective PCR-based molecular diagnostic systems. A device containing the present invention described is dipped into surface water in order to load a small amount of aqueous solution into the system. Alternatively, the device is submerged and water is autosampled via microfluidics at pre-programmed intervals. DNA is released from living material in the solution via bringing the system to a temperature in excess of 100° C. for a brief period (1-2 min). Several design options exist at this point including conducting this step in the same section of the MGCM pre-loaded with the PCR system. Current commercially available thermostable DNA polymerases can tolerate temperatures well above 100° C. Protein engineering is currently being applied to raise the thermal tolerance of these enzymes even to even higher levels. In addition, the *E. Coli* in the environment occurs in a wide array of physiological and physical states including damaged cells and cell debris that will easily release genome fragments to the external environment. The extraction procedure can be optimized as part of the device design. Once free DNA has been generated, the PCR reaction is initiated based on a thermal cycling sequence calculated from the length and GC content of the oligonucleotide primers. There are 4 bases in DNA: adenine (A), thymine (T), guanine (G), and cytosine (C). 'A' must pair with 'T' and 'G' with 'C', which is referred to as obligate base pairing. It is these base pairs that hold the 2 strands of DNA in the famous double helix. Likewise, it is base pairing that causes the short oligonucleotide primer to 'anneal' to a single stranded 'target' DNA molecule during PCR. GC pairs form three hydrogen bonds whereas AT pairs have only two. As a result, DNA with a higher GC content requires slightly more thermal energy to denature than DNA with a high AT content. After 20-30 cycles, the system is queried for accumulation of DNA. The query may occur photonically, spectrophotonically, via electromagnetic (EM), or surface plasmon resonance (SPR) methods. The latter method involves filling the glass pores with polymeric, highly polar DNA that will undoubtedly change the form of the evanescent wave generated when light is passed through the glass coating of the MGCM. Finally, it may be desirable to use detergent as well as heat to liberate the DNA from biological tissues or cells. A number of preparation chamber designs are visualized that use microfluidics to place the extraction buffer in contact with cells and remove the detergent solution post-extraction. A very simple method would employ a two-chamber design whereby the sample enters the first chamber, detergent solution is pumped in, and the system is heated to boiling for 1-5 minutes. The detergent solution is forced out through a low molecular weight cutoff filter. The sample preparation chamber retains the DNA. Water is then added and the contents of the preparation chamber are moved to the reaction chamber. Depending on the material to be extracted, a separate sample preparation chamber may or may not be required.

EXAMPLE 5

In vivo PCR application. Many microsurgical and diagnostic devices already incorporate fiber optics and lasers into their design. The placement of an MGCM into these systems would require minimal modification. In this example, the MGCM system is incorporated into a microsurgical device for surgical procedures designed to remove a cancerous tumor. During such a procedure, the question of complete removal of cancerous tissue must be addressed. Approximately 50% of all cancers express mutations of the protein p53 to abnormally high levels. The p53 protein is found in a cell nucleus and is crucial for proper control of cell division in cells having a nucleus. Conversely, p53 and its gene are leads for anti-cancer treatments. If the area around a solid tumor is probed during surgery to insure that all cancerous tissue had been removed, there is a 50% chance that the MGCM-based probe of the present invention would be loaded to conduct PCR detection of p53 (since 50% of all cancers overexpress p53 or some mutated version of p53. Otherwise, another MGCM-based probe would be selected that would search for some other gene associated with the specific cancer about which the operation revolves.

This gene is one of the most highly studied in the human genome. The sequence variability has been systematically characterized, including diagnostic single nucleotide polymorphisms (SNPs). The actual technology is similar to that of the environmental biosensor. The MGCM system is incorporated at the tip of the surgical probe and, at various times during the surgery and microscopic bits of tissue or even individual cells are drawn into a chamber with the MGCM system. The chamber is designed to function with the surgical device but a wide array of methods are available to actually cut or remove biological samples from surrounding tissue, and bring into contact with the MGCM in isolation from the patient. Once again heating to above 100° C. may be used to liberate and denature dsDNA with the subsequent application of PCR and detection methods as previously discussed. If the cancer in question is one known to overexpress p53, then the oligonucleotides to highly conserved p53 sequences are employed. Other cancers are known to overexpress other known oncogenes.

EXAMPLE 6

Environmental bioweapon sensor application. In principle, there is no difference between an MGCM sensor designed to sense the presence of living agents used for biological weapons and the environmental sensing described in Example 2. PCR provides a universal method of detection for any biological organism (living or dead) that retains its DNA or RNA genome. This applies to all known biological organisms with the exception of prions.

EXAMPLE 7

Industrial biotechnology application. The MGCM system described here is used to identify successful cloning events as part of an automated genetic engineering system. After genetic manipulation, it is necessary to assay for the presence of the cloned gene in the putative recombinant organism, cell, or tissue. An automated protocol is developed that is similar in design to the in vivo PCR detection system described in Example 5. For industrial biotechnology applications, the gene being cloned is usually sequenced so that specific oligonucleotide probes may be easily designed. Samples of the recombinant product (bacteria, cells, and the like) are removed from the automated cloning system as part of a total quality management (TQM) protocol and assayed in real-time for the presence of the desired gene.

Having thus described the invention in rather full detail, it will be understood that such detail need not be strictly adhered to but that various changes and modifications may suggest themselves to one skilled in the art, all falling within the scope of the present invention as defined by the subjoined claims.

What is claimed is:

1. A metallic glass-coated microwire having a metallic core, wherein said glass has a thermal contraction coefficient less than that of said metallic core by a preselected value, said preselected value being such that said glass is under residual compression, interfacial bonding between said glass and said metallic core is substantially uniform, and surface cracking and bond breaks between metal and glass are substantially prevented, said glass coating having a controllable amount and configuration of surface porosity defined by a plurality of pores in a surface of said glass coating and at least some of said pores being filled with reagents for PCR in order to detect specific biological species.

2. The metallic glass-coated microwire of claim 1, wherein said glass coating has a surface area and at least 5% surface porosity as determined by the surface area.

3. The metallic glass-coated microwire of claim 2, wherein said glass coating has a surface area and at least 20% surface porosity as determined by the surface area.

4. The metallic glass-coated microwire of claim 3, wherein said glass coating has a surface area and at least 50% surface porosity as determined by the surface area.

5. The metallic glass-coated microwire of claim 1, wherein said metallic core is comprised of an amorphous alloy.

6. The metallic glass-coated microwire of claim 5, wherein said glass coating has a surface area and at least 5% surface porosity as determined by the surface area.

7. The metallic glass-coated microwire of claim 6, wherein said glass coating has a surface area and at least 20% surface porosity as determined by the surface area.

8. The metallic glass-coated microwire of claim 7, wherein said glass coating has a surface area and at least 50% surface porosity as determined by the surface area.

9. An in vivo PCR device, incorporating the metallic glass-coated microwire of claim 8.

10. The metallic glass-coated microwire of claim 1, in which the metallic core is electrically conductive to enable its resistance heating as part of the PCR process.

11. The metallic glass-coated microwire of claim 1, in which the metallic core is ferromagnetic to enable its heating with a high frequency magnetic field as part of the PCR process.

12. A detector, incorporating the metallic glass-coated microwire of claim 1, and wherein highly polar materials of PCR affect the magnetic output of said metallic glass-coated microwire.

13. A biological species sensor comprising a metallic glass-coated microwire as recited by claim 1.

14. A metallic glass-coated microwire having a metallic core, wherein said glass has a thermal contraction coefficient less than that of said metallic core by a preselected value, said preselected value being such that said glass is under residual compression, interfacial bonding between said glass and said metallic core is substantially uniform, and surface cracking and bond breaks between metal and glass are substantially prevented, said glass coating having a controllable amount and configuration of surface porosity defined by a plurality of pores in a surface of said glass coating and at least some of said pores being filled with reagents for PCR in order to detect specific chemical species.

15. The metallic glass-coated microwire of claim 14, wherein said metallic core is comprised of an amorphous alloy.

16. The metallic glass-coated microwire of claim 15, in which the metallic core is electrically conductive to enable its resistance heating as part of the PCR process.

17. The metallic glass-coated microwire of claim 15, in which the metallic core is ferromagnetic to enable its heating with high frequency magnetic field as part of the PCR process.

18. A chemical species sensor comprising a metallic glass-coated microwire as recited by claim 14.

19. A method for producing a porous metallic glass-coated microwire, comprising the steps of:

a. selecting glass that will have multiple phases after heat treatment;
b. thereafter, preparing a metallic glass-coated microwire, wherein said coating comprises said glass;
c. heat-treating said glass for time at temperature sufficient to cause formation of multiple phases;
d. immersing said heat-treated, multi-phase glass in selected acid mixture; and
e. continuing step "d" until a desired level of glass porosity is achieved.

20. A process for making porous metallic glass-coated microwire, comprising the steps of:
a. selecting glass that will have multiple phases after heat treatment;
b. drawing a glass-coated microwire wherein the coating comprises said selected glass;
c. subjecting said glass-coated microwire to a post-drawing process comprising the steps of:

i. carrying out an acid evaporation/condensation process by placing the metallic glass-coated microwire in a buret containing a select mixture of sulfuric, hydrochloric, and nitric acids, followed by evaporation in a flask containing air, so that an acid/air mixture within the flask is heated to create acid vapor;
ii. heat treating said glass-coated microwire;
iii. continuing said heat treatment for at least 20 minutes at a temperature of about 450-700° C., to allow said acid vapor to flow continuously over said glass for substantially the entire period of said heat treatment until the desired level of glass porosity results; and
iv. cleansing said acid vapor in a condenser before it is liberated.

* * * * *